US012799635B2

(12) United States Patent
Kim et al.

(10) Patent No.: US 12,799,635 B2
(45) Date of Patent: Nov. 17, 2026

(54) APPARATUS FOR CONTINUOUS SPINNING OF COAGULATIVE POLYMERIC MICROFIBERS AND METHOD FOR CONTINUOUS SPINNING OF COAGULATIVE POLYMERIC MICROFIBERS USING THE SAME

(71) Applicants: POSTECH Research and Business Development Foundation, Pohang-si (KR); KYUNGPOOK NATIONAL UNIVERSITY HOSPITAL, Daegu (KR); Kyungpook National University Industry-Academic Cooperation Foundation, Daegu (KR)

(72) Inventors: Joon Won Kim, Pohang-si (KR); Jongkyeong Lim, Yeongju-si (KR); Jaechan Park, Daegu (KR)

(73) Assignees: POSTECH RESEARCH AND BUSINESS DEVELOPMENT FOUNDATION, Pohang-si (KR); KYUNGPOOK NATIONAL UNIVERSITY HOSPITAL, Daegu (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 407 days.

(21) Appl. No.: 18/383,088

(22) Filed: Oct. 24, 2023

(65) Prior Publication Data

US 2024/0133080 A1 Apr. 25, 2024
US 2024/0229301 A9 Jul. 11, 2024

(30) Foreign Application Priority Data

Oct. 24, 2022 (KR) ........................ 10-2022-0137644
Oct. 23, 2023 (KR) ........................ 10-2023-0142094

(51) Int. Cl.
*D01D 5/28* (2006.01)
*A61L 24/04* (2006.01)
(Continued)

(52) U.S. Cl.
CPC .............. *D01D 5/28* (2013.01); *A61L 24/043* (2013.01); *A61M 25/0026* (2013.01);
(Continued)

(58) Field of Classification Search
None
See application file for complete search history.

(56) References Cited

U.S. PATENT DOCUMENTS 5,851,508 A * 12/1998 Greff .................. A61K 49/0404 424/9.4
7,867,193 B2 1/2011 McKenna et al.
10,188,396 B2 1/2019 Folk et al.

FOREIGN PATENT DOCUMENTS

JP 4619789 1/2011
KR 10-2092725 3/2020
(Continued)

OTHER PUBLICATIONS

Yang et al. [Yang & Duo], Bioinspired Polymeric Helical and Super helical Microfibers via Microfluidic Spinning, Macromolecular Rapid Commun. 2019, 40, 1900111. (Year: 2019).*
(Continued)

*Primary Examiner* — Manuel A Mendez
(74) *Attorney, Agent, or Firm* — LEX IP MEISTER, PLLC

(57) ABSTRACT

Disclosed is an apparatus for continuous spinning of coagulative polymeric microfibers comprising an outer microcatheter, an inner microcatheter having a smaller diameter than the outer microcatheter and inserted inside the outer microcatheter, a double lumen part in which the outer microcath-
(Continued)

eter and the inner microcatheter are coaxially superimposed with a radially spaced interstitial space, and a single lumen part formed by the outer microcatheter from an end of the inner microcatheter to an end of the outer microcatheter. A core fluid supplied through an interior of the inner microcatheter comprises a coagulative polymeric fluid, and a sheath fluid supplied through the interstitial space comprises a fluid including saline, wherein the core fluid and the sheath fluid may be configured to flow coaxially in the single lumen part to generate and discharge a coagulative polymeric microfiber.

16 Claims, 8 Drawing Sheets

(51) Int. Cl.

| | |
|---|---|
| ***A61M 25/00*** | (2006.01) |
| ***D01D 4/02*** | (2006.01) |
| ***D01D 5/06*** | (2006.01) |

(52) U.S. Cl.

CPC ................. *D01D 4/02* (2013.01); *D01D 5/06* (2013.01); *A61L 2300/418* (2013.01); *A61M 2025/0004* (2013.01); *A61M 2025/0039* (2013.01); *A61M 2025/0042* (2013.01); *D10B 2509/00* (2013.01)

(56) References Cited

FOREIGN PATENT DOCUMENTS

| | | | | | |
|---|---|---|---|---|---|
| KR | 10-2125953 | | | 6/2020 | |
| KR | 10-2155957 | | | 9/2020 | |
| KR | 10-2020-0127489 | | | 11/2020 | |
| KR | 20200127486 | A | * | 11/2020 | ............... B32B 1/00 |
| KR | 10-2022-0114844 | | | 8/2022 | |
| KR | 102456586 | B1 | * | 10/2022 | ........ B01L 3/502707 |
| WO | 2016158388 | | | 10/2016 | |
| WO | WO-2020099190 | A1 | * | 5/2020 | ............. A61K 31/78 |

OTHER PUBLICATIONS

Onyx FDA Summary, Summary of safety and effectiveness Data, date: 2003. (Year: 2003).*

KR102456586B1_translation (Year: 2022).*

KR20200127489A_translation (Year: 2020).*

Jongkyeong Lim et al., "Embolization of Vascular Malformations via In Situ Photocrosslinking of Mechanically Reinforced Alginate Microfibers using an Optical-Fiber-Integrated Microfluidic Device", Advanced Materials, vol. 33, Issue 14, pp. 2006759 (Apr. 8, 2021), DOI: 10.1002/adma.202006759.

Jongkyeong Lim et al., "3D Vascular Replicas Composed of Elastomer-Hydrogel Skin Multilayers for Simulation of Endovascular Intervention", Advanced Functional Materials, vol. 30, Issue 50, pp. 2003395 (Dec. 15, 2020), DOI: 10.1002/adfm.202003395.

* cited by examiner

Diameter of microfiber

Filling ratio when filling artificial aneurysm

APPARATUS FOR CONTINUOUS SPINNING OF COAGULATIVE POLYMERIC MICROFIBERS AND METHOD FOR CONTINUOUS SPINNING OF COAGULATIVE POLYMERIC MICROFIBERS USING THE SAME

CROSS-REFERENCE TO RELATED APPLICATION

This application claims priority to and the benefit of Korean Patent Application No. 10-2023-0142094, filed on Oct. 23, 2023, and Korean Patent Application No. 10-2022-0137644, filed on Oct. 24, 2022, in the Korean Intellectual Property Office, the entire disclosure of which are incorporated herein by references for all purposes.

BACKGROUND OF THE INVENTION

(a) Field of the Invention

The present invention relates to an apparatus for continuous spinning of coagulative polymeric microfibers and a method for continuous spinning of coagulative polymeric microfibers using the apparatus.

(b) Description of the Related Art

A cerebral aneurysm is an abnormally inflated, balloon-like blood vessel caused by a weakening of a blood vessel wall of a brain artery, which, if left untreated, can rupture due to blood flow inside the cerebral aneurysm and cause death. Treatments for cerebral aneurysms include coil embolization and cerebral aneurysm embolization using liquid embolic material.

Coil embolization involves making a small hole in a femoral artery, confirming a path through angiography using a contrast agent, and accessing an affected area using a microcatheter and guide wire. Depending on the shape of the aneurysm, a stent, a balloon, or a microcatheter is placed at the entrance of the cerebral aneurysm, and then a platinum coil is pushed in to fill the inside of the cerebral aneurysm under X-ray visualization. When it is confirmed that there is no blood flow inside the cerebral aneurysm using a contrast agent, the stent, balloon, or microcatheter is removed.

Coil embolization uses a platinum coil to fill a cerebral aneurysm, preventing blood flow to the cerebral aneurysm and thus preventing it from rupturing. However, coil embolization has the problem of low filling levels due to the use of a metal coil with high mechanical strength. Poor filling can lead to rebleeding and rupture as blood flows to the affected area.

Cerebral aneurysm embolization using liquid embolic materials involves placing a microcatheter and a balloon into the affected area in the same manner as coil embolization, and then discharging liquid embolic materials from the microcatheter to fill the inside of the cerebral aneurysm and prevent blood flow.

The above information disclosed in this Background section is only for enhancement of understanding of the background of the invention, and therefore it may contain information that does not form the prior art that is already known in this country to a person of ordinary skill in the art.

SUMMARY OF THE INVENTION

The present invention has been made in an effort to provide an apparatus for continuous spinning of coagulative polymeric microfibers such that a coagulative polymeric fluid can precipitate within a microcatheter to discharge a coagulative microfiber.

The present invention has also been made in an effort to provide a method for continuous spinning of coagulative polymeric microfibers using the apparatus for continuous spinning of a coagulative polymeric microfiber.

However, the problems to be solved by the embodiments of the present invention are not limited to the above-mentioned problems and can be expanded in various ways within the scope of the technical idea included in the present invention.

An apparatus for continuous spinning of coagulative polymeric microfibers according to an embodiment includes: an outer microcatheter, an inner microcatheter having a smaller diameter than the outer microcatheter and inserted inside the outer microcatheter, a double lumen part in which the outer microcatheter and the inner microcatheter are coaxially superimposed with a radially spaced interstitial space, and a single lumen part formed by the outer microcatheter from an end of the inner microcatheter to an end of the outer microcatheter. A core fluid supplied through an interior of the inner microcatheter includes a coagulative polymeric fluid, and a sheath fluid supplied through the interstitial space includes a fluid including saline. The core fluid and the sheath fluid are configured to flow coaxially in the single lumen part to generate and discharge a coagulative polymeric microfiber.

The apparatus includes further a support secured between the outer microcatheter and the inner microcatheter to maintain a spacing between the outer microcatheter and the inner microcatheter.

The support includes a plurality of supports spaced apart from each other in a circumferential direction of the inner microcatheter.

An end of the support is disposed adjacent to an end of the inner microcatheter in the double lumen part.

The outer microcatheter and the inner microcatheter are made of a flexible material.

The apparatus includes further a hydrophilic hydrogel thin film coated on a surface of the outer microcatheter.

The hydrophilic hydrogel thin film is coated on the surface of the outer microcatheter located in the single lumen part.

The coagulative polymeric fluid includes an ethylene-vinyl alcohol copolymer (EVOH) solution or a polylactide-co-glycolide and polyhydroxyethylmethacrylate copolymer solution.

A method for continuous spinning of coagulative polymeric microfibers according to another embodiment uses an apparatus for continuous spinning of microfibers including an outer microcatheter, an inner microcatheter having a smaller diameter than the outer microcatheter and inserted inside the outer microcatheter, a double lumen part in which the outer microcatheter and the inner microcatheter are coaxially superimposed with a radially spaced interstitial space, and a single lumen part formed by the outer microcatheter from an end of the inner microcatheter to an end of the outer microcatheter.

The method includes: transferring a saline-based fluid as a sheath fluid through the interstitial space between an exterior of the inner microcatheter and an interior of the outer microcatheter, transferring a coagulative polymeric fluid as a core fluid through an interior of the inner microcatheter, generating a coagulative polymeric microfiber by allowing the saline-based fluid and the coagulative polymeric fluid to flow coaxially in contact with each other in the single lumen part, and discharging the coagulative polymeric microfiber from an end of the outer microcatheter of the single lumen part.

The coagulative polymeric fluid includes an ethylene-vinyl alcohol copolymer (EVOH) solution or a polylactide-co-glycolide and polyhydroxyethylmethacrylate copolymer solution.

A hydrophilic hydrogel thin film is coated on a surface of the outer microcatheter.

The hydrophilic hydrogel thin film is coated on the surface of the outer microcatheter located in the single lumen part.

An apparatus for continuous spinning of coagulative polymeric microfibers according to still another embodiment includes: an outer microcatheter, an inner microcatheter having a smaller diameter than the outer microcatheter and inserted inside the outer microcatheter, a double lumen part in which the outer microcatheter and the inner microcatheter are coaxially superimposed with a radially spaced interstitial space, a single lumen part formed by the outer microcatheter from an end of the inner microcatheter to an end of the outer microcatheter, and a hydrophilic hydrogel thin film coated on a surface of the outer microcatheter. A core fluid supplied through an interior of the inner microcatheter and a sheath fluid supplied through the interstitial space are configured to flow coaxially in the single lumen part to generate and discharge a coagulative polymeric microfiber.

The apparatus includes further a support secured between the outer microcatheter and the inner microcatheter to maintain a spacing between the outer microcatheter and the inner microcatheter.

The hydrophilic hydrogel thin film is coated on the surface of the outer microcatheter located in the single lumen part.

The core fluid includes an ethylene-vinyl alcohol copolymer (EVOH) solution or a a polylactide-co-glycolide and polyhydroxyethylmethacrylate copolymer solution, and the sheath fluid includes a fluid including saline.

According to an embodiment of the apparatus for continuous spinning of microfibers, an elongated coagulative polymeric liquid material guided by a sheath fluid inside the apparatus has short coagulation time due to a high surface area to volume ratio, which enables continuous spinning of polymeric microfibers without clogging.

According to an embodiment of the apparatus for continuous spinning of microfibers, since a microfiber is substantially fabricated in a single lumen part, the arrangement of the inner and outer microcatheters can be kept concentric thanks to two or more supports, even when bending occurs in the double lumen part, to form an elongated flow of coagulative polymeric liquid material.

In addition, since the apparatus for continuous spinning of microfibers completely coagulates the polymer microfibers inside and then moves them along a flow direction and discharges them out of the apparatus, polymer microfibers can be produced continuously regardless of the surrounding fluid. Therefore, the apparatus for continuous spinning of microfibers can embolize aneurysms by continuously producing polymeric microfibers even in a real blood-filled intravascular environment. The diameter of the polymeric microfibers produced can be adjusted by manipulating the flow rates of the core fluid and the sheath fluid.

Therefore, it can be applied to patients who have difficulty forming a thrombus by uniformly and completely embolizing the aneurysm in an impermeable manner, and it is possible to perform aneurysm embolization without a creation of fine fragments due to a leakage into a main artery during injection and without stenosis on the surface of the microcatheter.

DETAILED DESCRIPTION OF THE EMBODIMENTS

Figure 1:
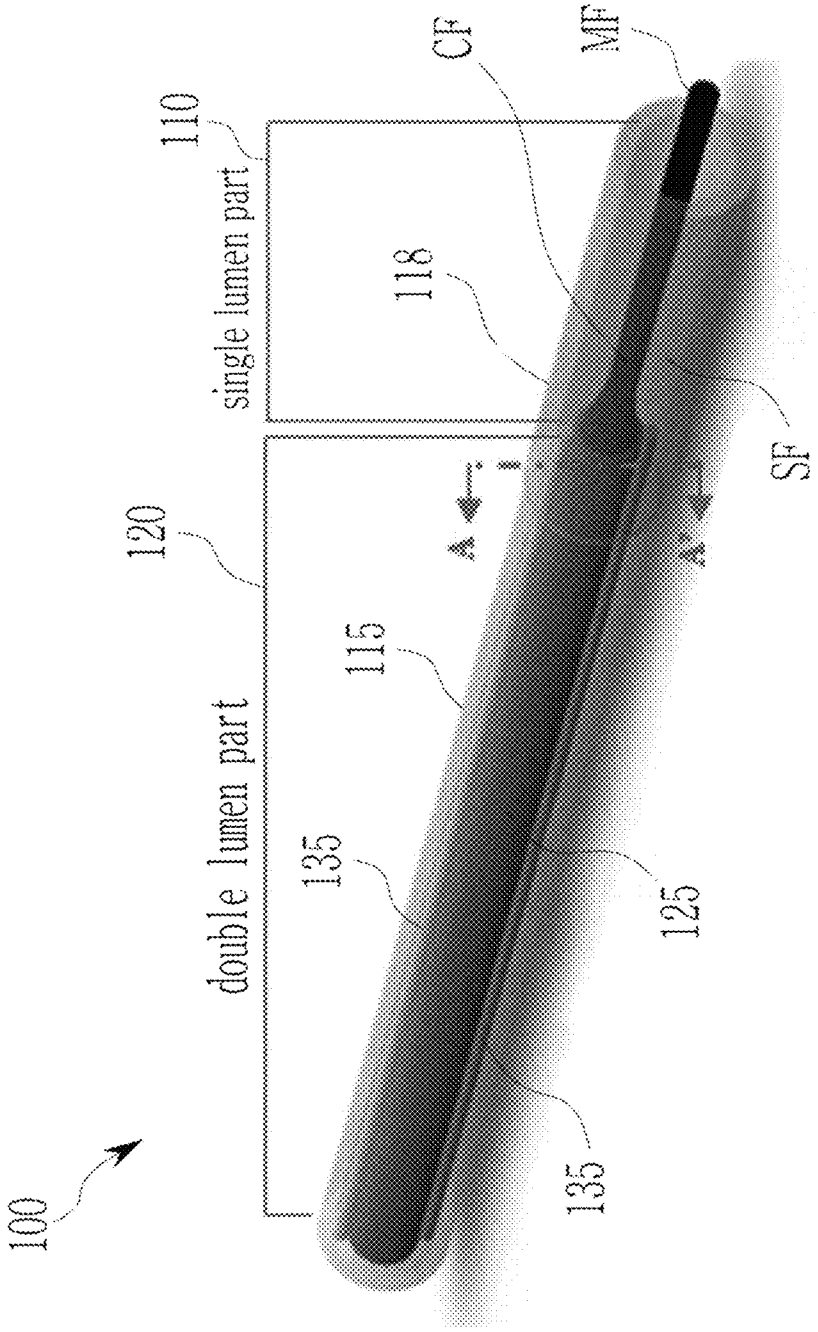
FIG. 1 is a perspective view of an apparatus for continuous spinning of coagulative polymeric microfibers according to an embodiment.

Embodiments of the present invention are hereinafter described in detail with reference to the accompanying drawings so that one of ordinary skill in the art to which the present invention belongs can readily practice it. In order to clearly illustrate the invention in the drawings, parts that are not relevant to the description have been omitted, and identical or similar elements are designated by the same reference numerals throughout the specification. In addition, in the accompanying drawings, some elements are exaggerated, omitted, or shown schematically, and the dimensions of each element are not intended to be entirely reflective of actual dimensions.

The accompanying drawings are intended only to facilitate an understanding of the embodiments disclosed herein, and it is to be understood that the technical ideas disclosed herein are not limited by the accompanying drawings and include all modifications, equivalents, or substitutions that are within the scope of the ideas and technology of the present invention.

Terms containing ordinal numbers, such as “first,” “second,” and the like, may be used to describe various elements, but the elements are not limited by such terms. These terms are used only to distinguish one element from another.

In addition, when an element such as a layer, a film, a region or a board is referred to as being “on” or “above” another element, the element may be “directly on” another element or may have a third element interposed therebetween. On the other hand, when an element is referred to as being “directly on” another element, there is no third element interposed therebetween. In addition, when an element is referred to as being “on” or “above” a reference element, the element may be disposed on or below the reference element, and may not necessarily be "on" or "above" the reference element in an opposite direction of gravity.

It should be understood that terms "include" and "comprise" used in the specification specify the presence of features, numerals, steps, operations, components, parts or combinations thereof, mentioned in this specification, and do not preclude the presence or addition of one or more other features, numerals, steps, operations, components, parts, or combinations thereof. Unless explicitly described to the contrary, "including" any component is to be understood to imply the inclusion of other components rather than the exclusion of other components.

Further, throughout the specification, an expression "on the plane" may indicate a case where a target is viewed from the top, and an expression "on the cross section" may indicate a case where a cross section of a target taken along a vertical direction is viewed from its side.

In addition, throughout the specification, when it is mentioned that any component is "connected" to another component, it may not only indicate that two or more components are directly connected with each other, but also indicate that two or more components are connected with each other indirectly through another component, may not only indicate that two or more components are physically connected with each other, but also indicate that two or more components are electrically connected with each other, or two or more components are a single entity although referred to by different names based on their dispositions or functions.

Figure 2:
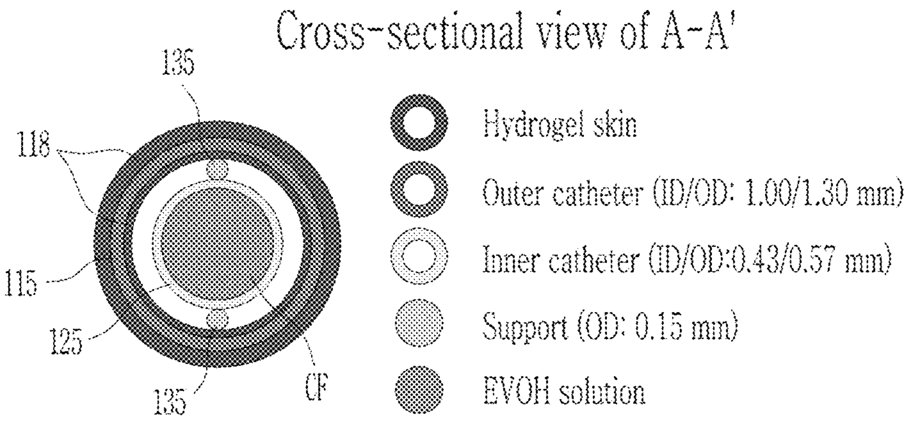
FIG. 2 is a cross-sectional view taken along line A-A' of FIG. 1.

FIG. 1 is a perspective view of an apparatus for continuous spinning of coagulative polymeric microfibers according to an embodiment, and FIG. 2 is a cross-sectional view taken along line A-A' of FIG. 1.

Referring to FIG. 1, the apparatus for continuous spinning of coagulative polymeric microfibers 100 (hereinafter also referred to as a "microfiber continuous spinning apparatus") according to the present embodiment includes an outer microcatheter 115, and an inner microcatheter 125 having a smaller diameter than that of the outer microcatheter 115 and inserted inside the outer microcatheter 115. The outer microcatheter 115 may be formed to have a first length, and the inner microcatheter 125 may be formed to have a second length that is shorter than the first length. Here, the first length and the second length may be lengths measured starting from a proximal end of a fluid inlet side of the outer microcatheter 115.

The microfiber continuous spinning apparatus 100 may include a double lumen part 120 including an outer microcatheter 115 and an inner microcatheter 125, and a single lumen part 110 including an outer microcatheter 115. The double lumen part 120 is where the outer microcatheter 115 and the inner microcatheter 125 overlap coaxially with a radially spaced interstitial space. The single lumen part 110 may be formed by the outer microcatheter 115 from an end of the inner microcatheter 125 to an end of the outer microcatheter 115, and is a portion made up of the outer microcatheter 115 without overlapping the inner microcatheter 125.

The outer microcatheter 115 and the inner microcatheter 125 may be made of flexible materials. For example, the outer microcatheter 115 and the inner microcatheter 125 can be made of silicone, polyurethane, polyethylene, Teflon®, polytetrafluoroethylene (PTFE), polyvinyl chloride (PVC), or other materials that are compatible with use in the human body. Furthermore, the inner microcatheter 125 can move freely inside the outer microcatheter 115, making it easy to manipulate the positions of the double lumen part 120 and the single lumen part 110 of the microfiber continuous spinning apparatus 100 and compatible with existing endovascular treatment methods utilizing microcatheters. The inner and outer microcatheters 125 and 115 can use any microcatheter materials of the art, for example, Marathon™, Rebar™ 10, Echelon™ 10, etc. for the inner microcatheter 125, and Rebar™ 27, Marksman™, Phenom™ 027, Glidecath®, etc. for the outer microcatheter 115.

Between the outer microcatheter 115 and the inner microcatheter 125 of the double lumen part 120, a support 135 may be inserted and secured to maintain a spacing between the outer microcatheter 115 and the inner microcatheter 125. The support 135 may include a plurality of supports, and the plurality of supports 135 may be spaced apart from each other circumferentially of the inner microcatheter 125. The support 135 may be disposed such that they do not protrude into the single lumen part 110, and to this end, the ends of the supports 135 may be disposed such that they are adjacent to or aligned with the ends of the inner microcatheter 125 in the double lumen part 120. The support 135 may be made of any flexible material compatible with use in the human body, such as silica, polyimide, silicone, polyurethane, polyethylene, Teflon®, polytetrafluoroethylene (PTFE), polyvinyl chloride (PVC), and the like. As another example, the support 135 fixed to the inner microcatheter 125 may use a known optical fiber, for example, Optran® UV fiber. As still another example, the support 135 may be manufactured integrally with the inner microcatheter 125 to perform its function.

A core fluid CF may be supplied to flow through the inner microcatheter 125, and a sheath fluid SF may be supplied to flow in the interstitial space between the inner microcatheter 125 and the outer microcatheter 115 located in the double lumen part 120. The core fluid CF and sheath fluid SF thus supplied may flow coaxially in the single lumen part 110 and may contact each other.

A coagulative polymeric fluid may be used as the core fluid CF, and a fluid including a saline solution may be used as the sheath fluid SF. The coagulative polymeric fluid may include an ethylene-vinyl alcohol copolymer (EVOH) solution or a polylactide-co-glycolide and polyhydroxyethylmethacrylate copolymer solution.

The surface of the outer microcatheter 115 may be coated with a hydrophilic hydrogel thin film 118. The hydrogel thin film 118 may be formed by coating an outer surface and an inner surface of the outer microcatheter 115 constituting the single lumen part 110. The hydrophilic hydrogel thin film 118 may reduce the adhesion between the coagulative polymeric fluid and the outer microcatheter 115. That is, when the coagulative polymeric fluid meets the outer microcatheter 115, the hydrophilicity of the hydrogel thin film 118 causes the outer microcatheter 115 to become wetted with water, and the coagulative polymeric fluid is separated.

Figure 3:
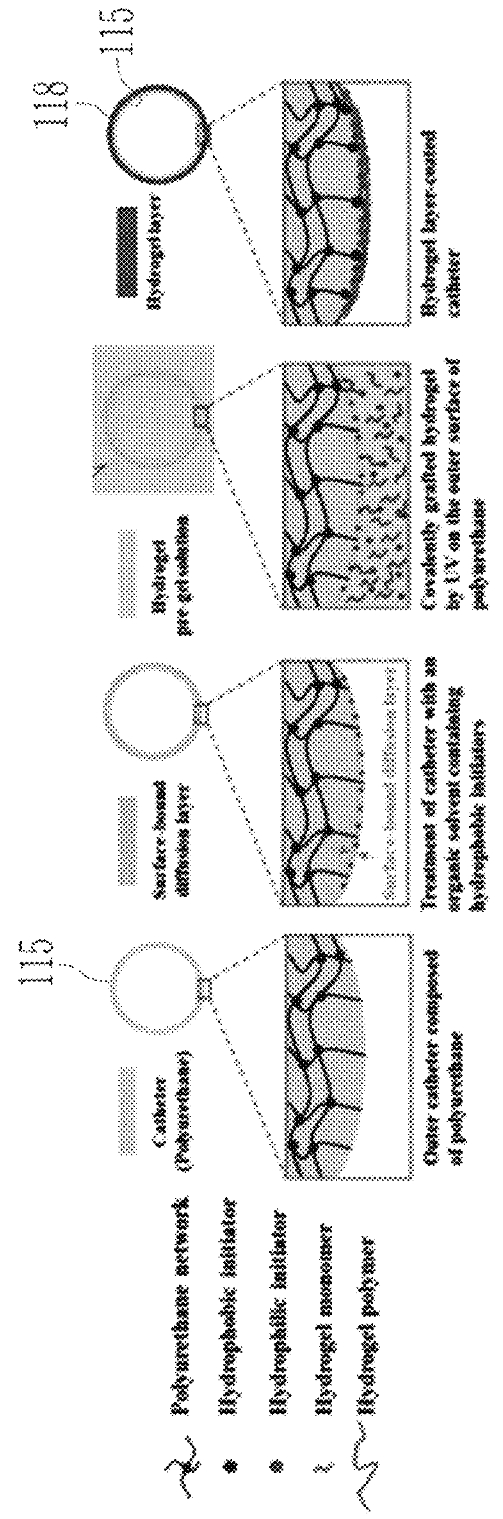
FIG. 3 is a diagram illustrating a method of forming a hydrogel thin film on an outer microcatheter of an apparatus for continuous spinning of coagulative polymeric microfibers according to an embodiment.

FIG. 3 is a diagram illustrating a method of forming a hydrogel thin film on an outer microcatheter of an apparatus for continuous spinning of coagulative polymeric microfibers according to an embodiment.

Referring to FIG. 3, first, in order to coat the outer microcatheter 115 of the microfiber continuous spinning apparatus 100 with a hydrogel thin film, the outer microcatheter 115 is immersed in a pretreatment solution. The hydrogel thin film may be pretreated so that it can be strongly bonded to the outer surface of the outer microcatheter 115. For example, an outer surface of the outer microcatheter 115 may be pretreated using benzophenone as a pretreatment solution.

Next, the pretreated outer microcatheter 115 is immersed in a hydrogel precursor solution. As a hydrogel precursor solution, a solution containing acrylamide may be used. Acrylamide serves to form a strong bond with the outer microcatheter 115 when irradiated with ultraviolet (UV) light.

Next, the outer microcatheter 115 immersed in the hydrogel precursor solution is cured by irradiating UV light to form a hydrogel thin film.

Figure 4:
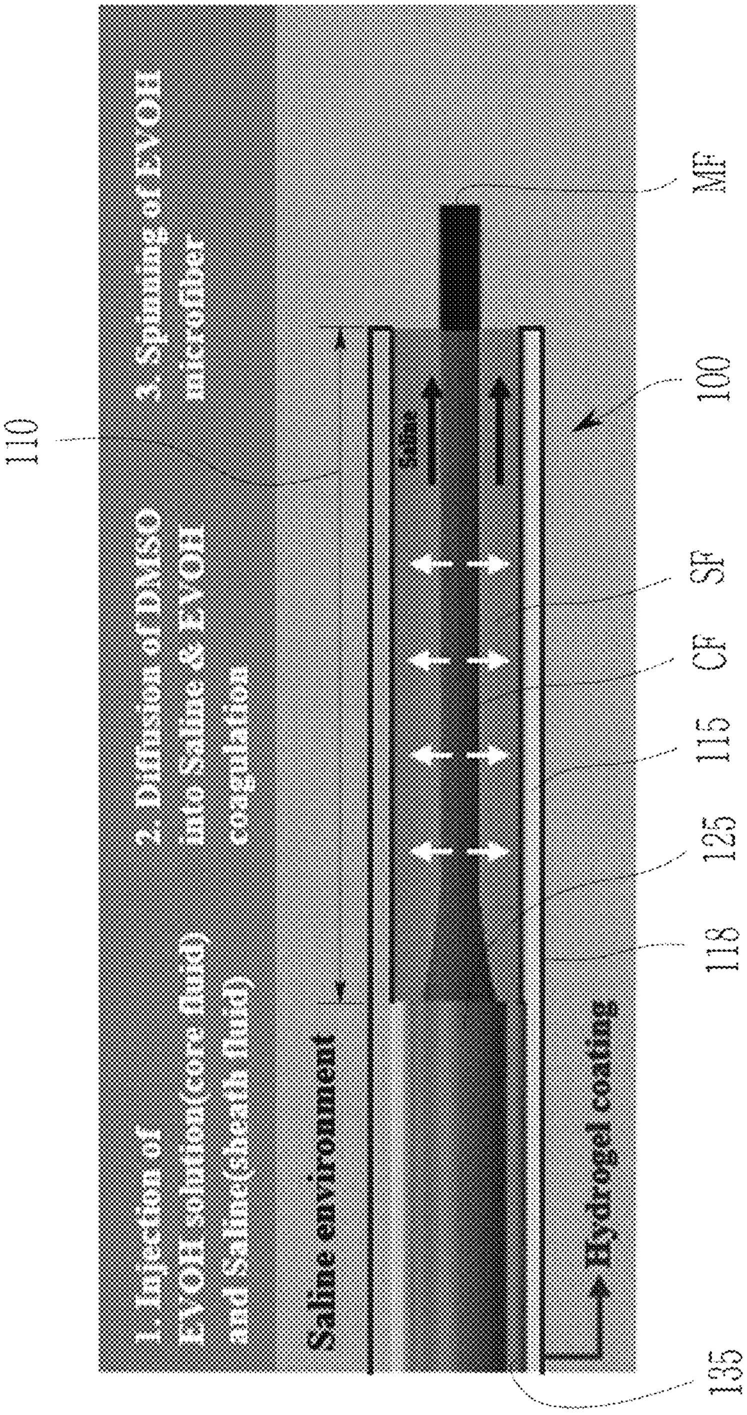
FIG. 4 is a diagram illustrating a method for continuous polymerization of microfibers using an apparatus for continuous spinning of coagulative polymer microfibers according to an embodiment.

FIG. 4 is a diagram illustrating a method for continuous polymerization of microfibers using an apparatus for continuous spinning of coagulative polymer microfibers according to an embodiment.

Referring now to FIG. 4, the principle of spinning coagulative polymeric liquid materials inside the microfiber continuous spinning apparatus 100 according to the present embodiment will be described.

By supplying a coagulative polymeric fluid, an ethylene vinyl alcohol (EVOH) solution, to flow as a core fluid CF through the inner microcatheter 125 of the microfiber continuous spinning apparatus 100 and a saline-based fluid to flow as a sheath fluid SF through the outer microcatheter 115, the core fluid CF and the sheath fluid SF can meet and join together in a single lumen part 110. At this point, the coagulative polymeric fluid can be dominated by laminar flow and diffusion, which are dominant phenomena at the microscale, to form an elongated flow by a 3D coaxial sheath flow stream formed around it. The elongated flow forms a large surface area relative to volume, which can reduce time for coagulative polymeric fluids to coagulate.

As the elongated coagulative polymeric fluid flows to the outlet of the microfiber continuous spinning apparatus 100, in situ precipitation, that is, continuous spinning of a moving liquid, can be achieved. Here, the coagulated polymeric microfibers MF may move along the flow direction without touching the inner surface of the outer microcatheter 115 and be discharged out of the microfiber continuous spinning apparatus 100.

For example, in order to solve the problem of low filling in existing cerebral aneurysm embolization, there are cases where cerebral aneurysms are treated with Medtronic's Onyx®, a liquid embolic material. Onyx® utilizes the principle that a dimethyl sulfoxide (DMSO) solution diffuses and causes dissolved EVOH to coagulate. However, with Onyx®, there is a risk that the solution filling the cerebral aneurysm may reflux and block a parent artery. In addition, when removing the microcatheter after completing embolization, there is concern about the possibility of occlusion of blood vessels due to the formation of microscopic fragments from the EVOH mass adhered to the microcatheter.

According to the microfiber continuous spinning apparatus 100 according to this embodiment, when saline solution is discharged from the outer microcatheter 115 and EVOH solution is discharged from the inner microcatheter 125, the EVOH solution is guided to the center by the saline solution. At this time, DMSO present in the EVOH solution diffuses into the saline solution, and coagulation hardening of EVOH begins. Through hardening, EVOH microfibers can be discharged, allowing them to flow straight and prevent backflow. Therefore, the EVOH microfibers do not escape into a parent artery, and the interior of the cerebral aneurysm can be filled to a high filling ratio due to the low mechanical strength of EVOH.

Furthermore, in the microfiber continuous spinning apparatus 100 according to the present embodiment, because microfibers are substantially fabricated in the single lumen part 110 according to the structure designed as described above, even if bending occurs in the double lumen part 120, the arrangement of the inner and outer microcatheters 125, 115 can remain in concentric circles thanks to the plurality of supports 135 to form an elongated flow of coagulative polymeric fluid.

Since the microfiber continuous spinning apparatus 100 according to the present embodiment completely agglomerates the coagulative polymeric microfibers inside and then moves them along the flow direction and discharges them out of the apparatus, the coagulative polymeric microfibers MF can be continuously produced regardless of the type of surrounding fluid. Therefore, the microfiber continuous spinning apparatus 100 according to this embodiment can embolize an aneurysm by continuously producing coagulative polymeric microfibers MF even in an actual intravascular environment filled with blood. The diameter of the produced polymeric microfibers MF can be adjusted by manipulating the flow rates of the core fluid and the sheath fluid.

The following describes in more detail examples of a microfiber continuous spinning apparatus and the results of experiments using the apparatus. However, it is not intended that the scope of the present invention be limited to the following examples.

Example 1. Fabrication of a Microfiber Continuous Spinning Apparatus with a Double-Lumen Structure To fabricate a microfiber continuous spinning apparatus, Echelon™ was used as an inner microcatheter and Glidecath® as an outer microcatheter. (1) First, a 0.6 mm×0.2 mm rectangular grooved substrate was prepared by 3D printing. (2) Next, using the 3D printed substrate, an inner microcatheter (Echelon™) with an inner diameter of 430 μm and an outer diameter of 570 μm was prepared, and two supports (Optran® UV fiber) with a diameter of 150 μm were arranged to be spaced apart in a circumferential direction of the inner microcatheter. Afterward, their ends were attached using epoxy (Scotch® super glue liquid). (3) Next, the inner microcatheter with the support attached was separated from the substrate and the support was cut so that it did not protrude from the end of the inner microcatheter. (4) Next, the inner microcatheter with the supports bonded side by side was inserted into the outer microcatheter (Glidecath®) with an inner diameter of 1000 μm and an outer diameter of 1300 μm, and the length of the single lumen part was maintained between 5.19 and 10 mm (see FIG. 2).

Example 2. Forming a Hydrogel Thin Film on an Outer Microcatheter

A hydrogel thin film was formed on the outer microcatheter of the double-lumen microfiber continuous spinning apparatus manufactured in Example 1. (1) First, a pretreatment solution was prepared by mixing benzophenone in ethanol at a concentration of 10% w/v. (2) Next, the microcatheter was immersed in the pretreatment solution for 2 minutes, then washed thoroughly with isopropyl alcohol, and the surface was dried with nitrogen. (3) Next, a hydrogel precursor solution was prepared by mixing acrylamide at a concentration of 10% w/v and Irgacure® 2959 at a concentration of 1% w/v in water. (4) Next, the pretreated microcatheter was immersed in the hydrogel precursor solution and then irradiated with UV light (365 nm) for about 1 hour to harden the hydrogel. (5) Next, the remaining residue, excluding the hydrogel thin film formed on the surface, was thoroughly washed with ultrapure water to complete the formation of the hydrogel thin film on the surface of the microcatheter.

Figure 5:
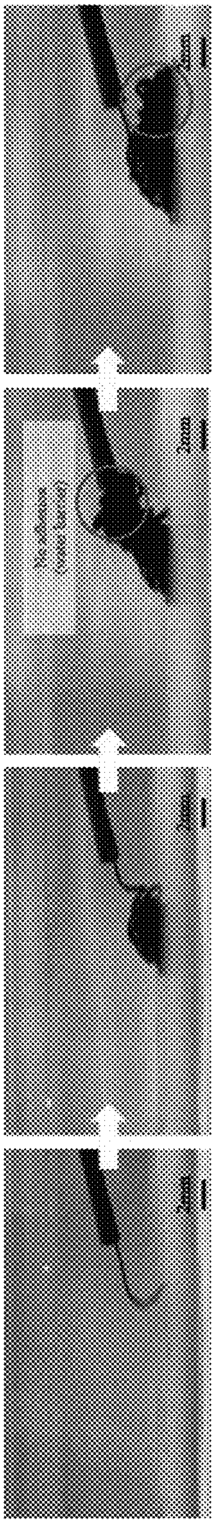
FIG. 5 is an image showing results of continuous spinning of coagulative polymeric microfibers when water is a sheath fluid using an apparatus for continuous spinning of coagulative polymeric microfibers according to an embodiment.
Figure 6:
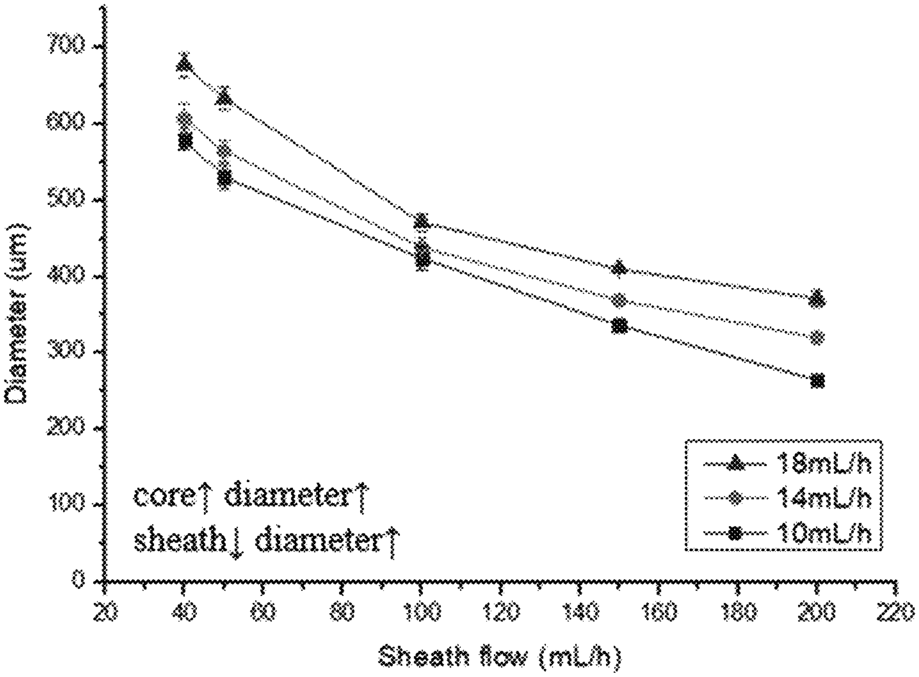
FIG. 6 is a graph showing changes in diameter of continuously spun coagulative polymeric microfibers depending on the flow rates of core fluids and sheath fluids.

Example 3. Continuous Polymerization of Coagulative Polymeric Microfibers Using a Double-Lumen Microfiber Continuous Spinning Apparatus Coagulative polymeric microfibers were continuously polymerized using the double-lumen structure microfiber continuous spinning apparatus manufactured in Example 1, and the results are shown in FIGS. 5 and 6.

The core flow rate (flow rate of the core fluid) was manipulated between 5 mL/h and 20 mL/h. 5 mL/h is the flow rate that can fill an empty space of a 7 mm diameter sphere within 3 minutes and 20 mL/h is the flow rate that does not exceed the allowable pressure of the inner microcatheter. Brain cells begin to die if they are not supplied with blood for 3 minutes. The sheath flow rate (flow rate of the sheath fluid) was manipulated at more than or equal to 40 mL/h, which allows the coagulative polymeric fluid to form an elongated flow within the range of the previously determined core flow rate.

The double-lumen microfiber continuous spinning apparatus constructed as described above has a large surface area to volume ratio to sufficiently crosslink the elongated polymeric liquid material. Coagulative polymer microfibers had a diameter of about 300 μm to 700 μm, and generally, the diameter of the microfibers tended to increase as the core flow rate increased and the sheath flow rate decreased. This is because the diameter of the single lumen part is fixed, so as the flow rate of either the core fluid or the sheath fluid increases, the space occupied also increases.

Meanwhile, in the microfiber continuous spinning apparatus, since the microfibers are substantially fabricated in a single lumen part, even when bending occurs in the double lumen part, the arrangement of the inner and outer microcatheters remains concentric thanks to the supports, allowing the coagulative polymeric fluid to form an elongated flow.

Example 4. Experiment with Filling of Polymeric Microfibers within a Coronary Aneurysm Model Experiments with the filling of polymeric microfibers within a coronary aneurysm model containing an aneurysm (i.e., a spherical void) were evaluated as a "proof of concept" for aneurysm embolization. The coronary aneurysm model used in these experiments was composed of elastomer-hydrogel skin multilayers that closely mimic the geometry and properties of blood vessels. An image showing the experimental setup with a vessel replica, balloon, pulsating pump, and fluid reservoir is shown in FIG. 7.

Blood-like fluid is circulated inside the coronary aneurysm model with the help of a pulsating pump (Model 1405, Harvard Apparatus) and transferred to the fluid reservoir through a filter system (20 μm mesh). The filter system can check whether micro-debris (microscopic fragments) is generated during the simulated procedure.

Figure 7:
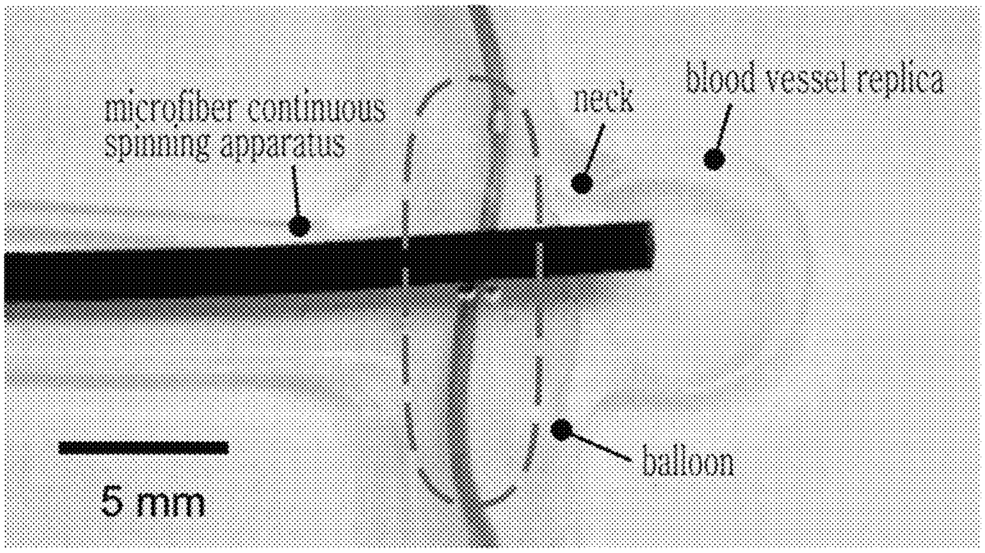
FIG. 7 is an image showing an experimental device equipped with a blood vessel replica and a balloon.

The process of filling a 7 mm diameter aneurysm within a coronary vessel replica with polymeric microfibers is shown in FIG. 7. (1) A tip of the microfiber continuous spinning apparatus was placed at the entrance of the aneurysm, and a balloon microcatheter (Scepter CTM, BC0410C, Microvention) was placed across a neck of the aneurysm to temporarily block the entrance of the aneurysm and then inflated. (2)-(3) The polymeric microfibers continuously discharged from the apparatus in a connected form gradually fill the aneurysm, and the inflated balloon prevents the polymeric microfibers from flowing out of the aneurysm below a certain filling rate. (4) After filling the aneurysm to the maximum extent possible, until the microfibers pass through the gap between the balloon, the apparatus, and the aneurysm neck and are about to flow out of the aneurysm, the apparatus was turned off. Finally, the procedure was completed by removing the apparatus and the balloon microcatheter from the coronary aneurysm model.

To investigate the maximum amount of polymeric microfibers that can fill an aneurysm, an experiment was conducted while manipulating core flow/sheath flow rates. Here, the maximum filling ratio was calculated as the amount of polymeric microfibers injected just before leaking out of the aneurysm (core flow rate×discharge time) compared to the internal volume of the aneurysm. Extravasation of polymeric microfibers from the aneurysm occurs when the pressure inside the aneurysm is greater than the force that the microfibers resist in the gap between the balloon, apparatus, and aneurysm neck. To determine the effect of sheath flow rate on filling ratio and filling time, a filling experiment was conducted while fixing the core flow rate of 10, 14, and 18 mL/h and increasing the sheath flow rate.

Figure 8:
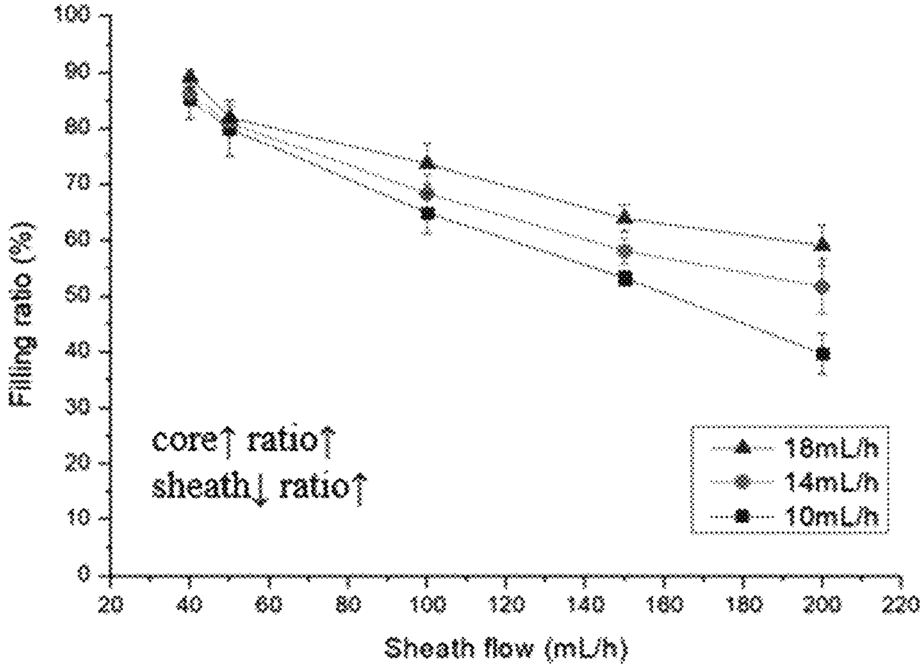
FIG. 8 is a graph showing filling ratios depending on the flow rates of core fluids and sheath fluids.

For the core flow rate of 10 mL/h, the filling ratio decreased from about 85% to about 40% as the sheath flow rate increased from 40 mL/h to 200 mL/h (see FIG. 8). This is because as the sheath flow rate increases, the internal pressure increases and the diameter of the microfiber becomes thinner, which reduces the resistance force of the microfiber in the gap between the balloon, apparatus, and aneurysm neck. Additionally, when the sheath flow rate was constant, the filling ratio tended to increase as the core flow rate increased (see FIG. 8). This is because the diameter of the microfiber became thicker as the core flow rate increased, and the resistance force of the microfiber in the gap between the balloon, apparatus, and aneurysm neck increased.

No blockage occurred in all tested conditions, and no micro-debris leaked out of the aneurysm. For 1 hour of circulating blood-like fluid at a flow rate of 280 mL/min at 70 Hz, there was no change in the shape of the polymeric microfibers filling the aneurysm. Because the polymeric microfibers contain 30% w/v tantalum nanopowders, they are opaque to X-rays, which can be used to localize the polymeric microfibers during the endovascular intervention to determine whether the aneurysm has been filled correctly.

While the foregoing describes preferred embodiments of the present invention, it is to be understood that the invention is not limited thereto, and that various modifications are possible and fall within the scope of the claims, the description, and the accompanying drawings.

What is claimed is:

1. An apparatus for continuous spinning of coagulative polymeric microfibers comprising:

an outer microcatheter;

an inner microcatheter having a smaller diameter than the outer microcatheter and inserted inside the outer microcatheter;

a double lumen part in which the outer microcatheter and the inner microcatheter are coaxially superimposed with a radially spaced interstitial space; and a single lumen part formed by the outer microcatheter from an end of the inner microcatheter to an end of the outer microcatheter, wherein a core fluid supplied through an interior of the inner microcatheter includes a coagulative polymeric fluid comprising a polymer solution in which a polymer is dissolved in a solvent, and a sheath fluid supplied through the interstitial space includes a fluid including saline, wherein the core fluid and the sheath fluid are configured to flow coaxially in the single lumen part such that the solvent diffuses into the sheath fluid to coagulate the coagulative polymeric fluid in the single lumen part, to generate and discharge a coagulative polymeric microfiber.

2. The apparatus for continuous spinning of coagulative polymeric microfibers of claim 1, further comprising a support secured between the outer microcatheter and the inner microcatheter to maintain a spacing between the outer microcatheter and the inner microcatheter.

3. The apparatus for continuous spinning of coagulative polymeric microfibers of claim 2, wherein the support comprises a plurality of supports spaced apart from each other in a circumferential direction of the inner microcatheter.

4. The apparatus for continuous spinning of coagulative polymeric microfibers of claim 2, wherein an end of the support is disposed adjacent to an end of the inner microcatheter in the double lumen part.

5. The apparatus for continuous spinning of coagulative polymeric microfibers of claim 1, wherein the outer microcatheter and the inner microcatheter are made of a flexible material.

6. The apparatus for continuous spinning of coagulative polymeric microfibers of claim 1, further comprising a hydrophilic hydrogel thin film coated on a surface of the outer microcatheter.

7. The apparatus for continuous spinning of coagulative polymeric microfibers of claim 6, wherein the hydrophilic hydrogel thin film is coated on an outer surface of the outer microcatheter constituting the single lumen part.

8. The apparatus for continuous spinning of coagulative polymeric microfibers of claim 1, wherein the coagulative polymeric fluid comprises an ethylene-vinyl alcohol copolymer (EVOH) solution or a polylactide-co-glycolide and polyhydroxyethylmethacrylate copolymer solution.

9. A method for continuous spinning of coagulative polymeric microfibers using an apparatus for continuous spinning of microfibers comprising an outer microcatheter, an inner microcatheter having a smaller diameter than the outer microcatheter and inserted inside the outer microcatheter, a double lumen part in which the outer microcatheter and the inner microcatheter are coaxially superimposed with a radially spaced interstitial space, and a single lumen part formed by the outer microcatheter from an end of the inner microcatheter to an end of the outer microcatheter, the method comprising:

transferring a saline-based fluid as a sheath fluid through the interstitial space between an exterior of the inner microcatheter and an interior of the outer microcatheter;

transferring a coagulative polymeric fluid comprising a polymer solution in which a polymer is dissolved in a solvent as a core fluid through an interior of the inner microcatheter;

generating a coagulative polymeric microfiber by allowing the saline-based fluid and the coagulative polymeric fluid to flow coaxially in contact with each other in the single lumen part such that the solvent diffuses into the saline-based fluid to coagulate the coagulative polymeric fluid in the single lumen part; and discharging the coagulative polymeric microfiber from an end of the outer microcatheter of the single lumen part.

10. The method for continuous spinning of coagulative polymeric microfibers of claim 9, wherein the coagulative polymeric fluid comprises an ethylene-vinyl alcohol copolymer (EVOH) solution or a polylactide-co-glycolide and polyhydroxyethylmethacrylate copolymer solution.

11. The method for continuous spinning of coagulative polymeric microfibers of claim 9, wherein a hydrophilic hydrogel thin film is coated on a surface of the outer microcatheter.

12. The method for continuous spinning of coagulative polymeric microfibers of claim 11, wherein the hydrophilic hydrogel thin film is coated on an outer surface of the outer microcatheter constituting the single lumen part.

13. An apparatus for continuous spinning of coagulative polymeric microfibers comprising:

an outer microcatheter;

an inner microcatheter having a smaller diameter than the outer microcatheter and inserted inside the outer microcatheter;

a double lumen part in which the outer microcatheter and the inner microcatheter are coaxially superimposed with a radially spaced interstitial space;

a single lumen part formed by the outer microcatheter from an end of the inner microcatheter to an end of the outer microcatheter; and a hydrophilic hydrogel thin film coated on a surface of the outer microcatheter, wherein a core fluid supplied through an interior of the inner microcatheter includes a coagulative polymeric fluid and a sheath fluid supplied through the interstitial space are configured to flow coaxially in the single lumen part to generate and discharge a coagulative polymeric microfiber, wherein the hydrophilic hydrogel thin film reduces adhesion between the coagulative polymeric fluid and the outer microcatheter.

14. The apparatus for continuous spinning of coagulative polymeric microfibers of claim 13, further comprising a support secured between the outer microcatheter and the inner microcatheter to maintain a spacing between the outer microcatheter and the inner microcatheter.

15. The apparatus for continuous spinning of coagulative polymeric microfibers of claim 13, wherein the hydrophilic hydrogel thin film is coated on an outer surface of the outer microcatheter constituting the single lumen part.

16. The apparatus for continuous spinning of coagulative polymeric microfibers of claim 13, wherein the core fluid comprises an ethylene-vinyl alcohol copolymer (EVOH) solution or a polylactide-co-glycolide and polyhydroxyethylmethacrylate copolymer solution, and wherein the sheath fluid comprises a fluid including saline.

* * * * *